US010634629B2

(12) United States Patent
Saxena et al.

(10) Patent No.: US 10,634,629 B2
(45) Date of Patent: Apr. 28, 2020

(54) TECHNIQUES FOR USING OXIDE THICKNESS MEASUREMENTS FOR PREDICTING CRACK FORMATION AND GROWTH HISTORY IN HIGH-TEMPERATURE METALLIC COMPONENTS

(71) Applicant: BOARD OF TRUSTEES OF THE UNIVERSITY OF ARKANSAS, Little Rock, AR (US)

(72) Inventors: Ashok Saxena, Fayetteville, AR (US); Ralph Edward Huneycutt, IV, Kansas City, MO (US); Kee Bong Yoon, Kyung-gi (KR)

(73) Assignees: Board of Trustees of the University of Arkansas, Little Rock, AR (US); Chun-Ang University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 15/987,772

(22) Filed: May 23, 2018

(65) Prior Publication Data
US 2018/0340897 A1 Nov. 29, 2018

Related U.S. Application Data

(60) Provisional application No. 62/510,335, filed on May 24, 2017.

(51) Int. Cl.
*G01N 23/2251* (2018.01)
*G01N 33/20* (2019.01)
*G01N 33/00* (2006.01)

(52) U.S. Cl.
CPC ........ *G01N 23/2251* (2013.01); *G01N 33/20* (2013.01); *G01N 2033/0096* (2013.01); *G01N 2223/405* (2013.01); *G01N 2223/418* (2013.01); *G01N 2223/601* (2013.01); *G01N 2223/61* (2013.01); *G01N 2223/624* (2013.01)

(58) Field of Classification Search
CPC .............. G01N 23/2251; G01N 33/20; G01N 2033/0096; G01N 2223/405; G01N 2223/418; G01N 2223/601; G01N 2223/61; G01N 2223/624
USPC ................. 250/305, 306, 307, 309, 310, 311
See application file for complete search history.

(56) References Cited

U.S. PATENT DOCUMENTS

| 5,766,971 A * | 6/1998 | Ahlgren | H01L 21/31116 438/296 |
| 2006/0292386 A1* | 12/2006 | Itou | F01L 3/02 428/469 |
| 2014/0241011 A1* | 8/2014 | Nomura | H01F 27/22 363/13 |

OTHER PUBLICATIONS

Ralph E. Huneycutt, IV, Feasibility of using Oxide Thickness Measurements for Predicting Crack Growth Rates in P91 Steel Components, MS Thesis, University of Arkansas, Apr. 2017.
(Continued)

*Primary Examiner* — Nicole M Ippolito
(74) *Attorney, Agent, or Firm* — Keith A Vogt, Ltd.; Keith A. Vogt

(57) ABSTRACT

A method and system to develop the age and history of a crack by exposing a specimen or component to varying predetermined temperature range that covers the designated service temperatures and measuring the thickness of the oxide across the specimen along the thickness direction.

14 Claims, 1 Drawing Sheet

(56) References Cited

OTHER PUBLICATIONS

A. Saxena, P.K. Liaw, and W.A. Logsdon, Residual Life Prediction and Retirement for Cause Criteria for SSTG Upper casings, Part II: Fracture Mechanics Analysis, Engineering Fracture Mechanics, vol. 25, 1986, pp. 289-303.
A. Saxena, Nonlinear Fracture Mechanics for Engineers, 16 pages; CRC Press, 1999.
A. Saxena editor, Comprehensive Structural Integrity, vol. 5—Creep, 2003.
K.B. Yoon and A. Saxena, "An Interpretation of ΔJ for Cyclically Unsaturated Materials," International Journal of Fracture, Jul. 1991.
K.B. Yoon, A. Saxena and P.K. Liaw, "Characterization of Creep-Fatigue Crack Growth Behavior Under Trapezoidal Waveshape Using Ct—Parameter," International Journal of Fracture, vol. 59, 1993, pp. 95-114.
L.W. Pinder, "Oxide Characterization for Service Failure Investigations", Corrosion Science, vol. 21, No. 11, pp. 749-763, 1981.
E. Tasdighi H. Nobakhti N. Soltani; "Application of Small Punch Test in Predicting the Axial Fatigue Life of 304 Stainless Steel Sheets"; SEM; Experimental Techniques (2015); Society for Experimental Mechanics.

* cited by examiner

TECHNIQUES FOR USING OXIDE THICKNESS MEASUREMENTS FOR PREDICTING CRACK FORMATION AND GROWTH HISTORY IN HIGH-TEMPERATURE METALLIC COMPONENTS

RELATED APPLICATIONS

This application claims the benefit of U.S. Provisional Application No. 62/510,335 filed May 24, 2017 and herein incorporated by reference.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BRIEF SUMMARY OF THE INVENTION

The present invention provides unique techniques for predicting the history of both crack formation and crack growth in components. Oxidation kinetics of ASTM Grade P91 Steel were characterized in the temperature range of 600° C. to 650° C. with exposure times ranging from 10 to 1000 hours utilizing weight gain measurements.

Oxide thickness as a function of temperature and exposure time was also measured on the oxidized samples using a scanning electron microscope.

The weight gain and thickness measurement data were used to determine the parabolic rate constant ($k_p$) as a function of temperature for this steel as a part of model development.

The value of $k_p$ and oxide thickness measurements from compact type specimens used in creep-fatigue crack growth experiments were used to predict the crack growth rates and were subsequently compared to the measured crack growth rates.

The predicted and measured crack growth rates were found to agree (within a factor of 2). This level of accuracy is considered very satisfactory in these applications.

In yet other embodiments of the present invention, even more accurate predictions can be made. As part of fractographic studies, the measurement of oxide thicknesses in creep and creep-fatigue crack growth specimens with a known crack growth history can be routinely performed and reported with crack growth data.

Other embodiments of the present invention provide a system and method for predicting the remaining life, safe inspection intervals and inspection criteria for high-temperature components. Thus, the embodiments of the present invention may be used to extend the life of expensive power plant systems and components.

The embodiments of the present invention may also be used to extend the life of land-based gas turbines and aircraft engines by reducing components that are prematurely retired.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Figure 1A:
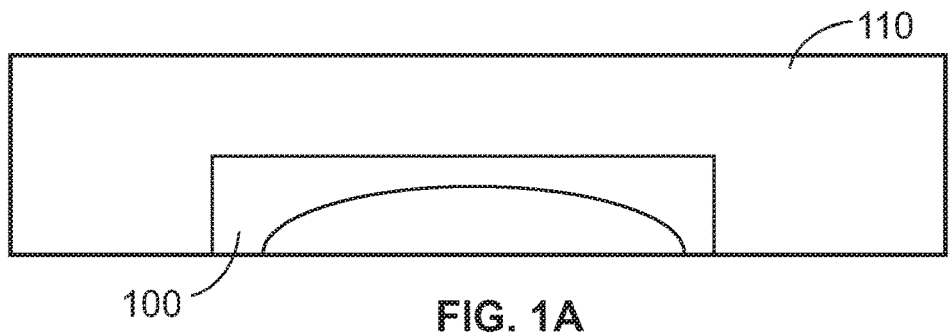
FIGS. 1A and 1B illustrate a method that may be used for an embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

Metal surfaces on various components are known to oxidize in air when exposed to high temperatures. Components subject to oxidation include reheat steam pipes, steam turbine rotors and casings, chemical reactors, land-based as well as aircraft turbine components in the hot-gas path. Oxidation leads to the development of cracks in these components due to creep-fatigue and creep mechanisms. Oxide thickness, x, on the surface of the crack is related to the exposure time, t, by the following equation:

$$x = \sqrt{k_p t} \tag{1}$$

$$\text{Where, } k_p = k_{p0} \exp - \frac{Q}{RT} \tag{2}$$

Metal Equation (1) is called the parabolic oxidation rate equation. Further, R in equation 2 is the universal gas constant, Q is the activation energy characteristic of the thermally activated, rate controlling process, and T is the temperature in degrees Kelvin. In one embodiment, the present invention pertains to the use of this relationship for predicting the age of cracks in high-temperature components and the rates at which the cracks have been growing during service.

In a preferred embodiment, the present invention provides a system and method to develop the age and history of cracks. The uniqueness of the invention lies in several of the following unique process and analytical steps used to develop the age and history of cracks:

1. Expose several rectangular specimens of well-polished specimens to temperatures in the range that cover the typical service temperatures for varying periods ranging between 10 and 1000 hours.
2. Cover the oxidized surface with a conductive resin to protect the oxide layer from spallation. Next, the specimen is sectioned to reveal the thickness of the oxide layer.
3. Measure the thickness of the oxide by SEM imaging and chemical mapping across the specimen along the thickness direction.
4. Software, such as MATLAB code, may be used, to automate the oxide thickness measurements at several locations and obtain a reliable measure of the average oxide thickness.
5. Equation (1) is fitted to the data to obtain the values of $k_{p0}$ and Q.

In other preferred embodiments, the present invention provides a system and method to estimate the age of cracks discovered in service. Plastic replicas of the cracked region may be used to estimate the oxide thickness at the mouth of the crack which is directly related to the age of the crack. If the crack is excavated from the component and the oxide thickness profile measured, the rate at which the crack was growing during service can be estimated. Thus, the full growth history of the cracks can be revealed and then used to validate analytical models used to estimate remaining life and inspection intervals in these components. The various steps in the technique are explained in more depth below.

Figure 1B:
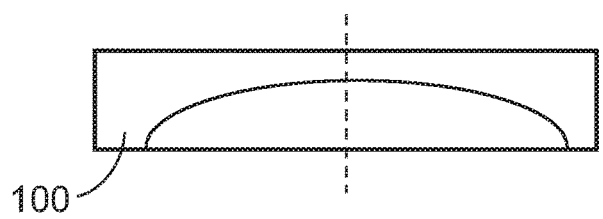

As shown in FIG. 1, the first step is to excavate cracked region 100 from component 110.

Next the excavated region is fractured to expose the crack surface so that coating 120 may be applied to protect the crack surface. Fracturing may be accomplished by dipping the excavated region in liquid Nitrogen or some other cold medium that will cause fracturing. Coating may be done by epoxy or Ni may be used by electroplating or vapor deposition.

Figure 2:
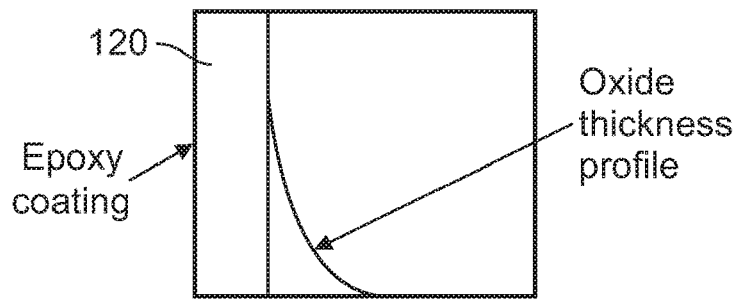
FIG. 2 illustrates another method that may be used for an embodiment of the present invention.

Next the coat excavated region is sectioned in half in the middle to reveal the oxide thickness profile 200 as shown in FIG. 2.

Oxide thickness, x, may be measured as a function of crack depth, $\Delta a$. $x_0$ is the oxide thickness at the mouth of the crack that may also be measured on the surface using of plastic replicas.

Figure 3:
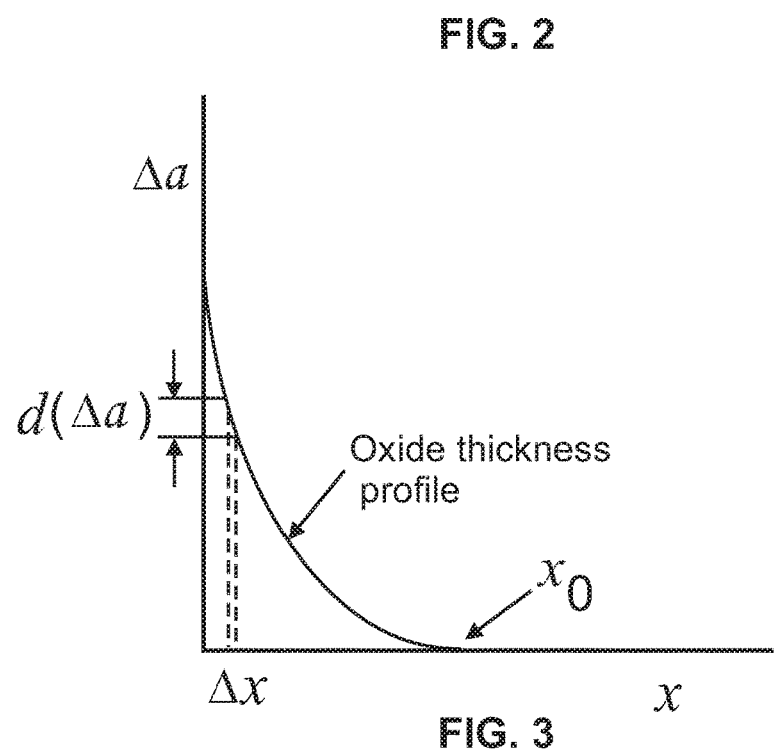
FIG. 3 shows the measured oxide thickness profile on the crack surface.

More detailed relationships between the oxide thickness measured on surfaces of cracks found in service and their time-history are given below and are shown in FIG. 3.

The age of the crack may be determined using the following equation:

$$t_f = \frac{x_0^2}{k_p}$$

Exposure time, t, may be determined using the following equation:

$$t = t_f - t' = \frac{x^2}{k_p}$$

Crack growth rate at any point on the crack surface may be determined using the below three equations:

Equation 1 is the governing equation for estimating crack growth rate:

$$\frac{d(\Delta a)}{dt'} = \frac{da}{dt'} = -\frac{k_p}{2x}\frac{d(\Delta a)}{dx} = -\frac{k_p}{2x(dx/d(\Delta a))}$$

Where, $\Delta a$=crack extension, t=exposure time=$t_f$-t', and t'=is the time referenced to the beginning of crack extension.

$$\frac{d(\Delta a)}{dx}$$

is negative so $$\frac{da}{dt'}$$

is positive. The estimation of $$\frac{d(\Delta a)}{dt'}$$

is schematically shown in FIG. 3.

The below equations may be used in computer algorithms using the equations below to generate the entire crack growth history of the component:

$$\Delta a_i = \int_{(t_f-t'_{i-1})}^{(t_f-t'_i)} \sqrt{\frac{k_p}{4(t_f-t')}} \, d(t_f-t')$$

$$\Delta a_i = \int_{\Delta a_{i-1}}^{\Delta a_i} d(\Delta a) = \int_{t'_{i-1}}^{t'_i} \left(-\frac{k_p}{2x}dt'\right)$$

$$\Delta a_i = \sqrt{k_p}\,[(t_f-t'_i)^{1/2} - (t_f-t'_{i-1})^{1/2}]$$

$$\Delta a(t'_i) = \Delta a(t'_{i-1}) + \Delta a_i$$

$$x = \sqrt{k_p(t_f-t')}$$

$$\Delta t' = \frac{t_f}{n}, \text{ where } n \text{ is an integer for appropriate time increments}$$

$$\Delta a_i = \int_{t'_{i-1}}^{t'_i} -\sqrt{\frac{k_p}{4(t_f-t')}} \, dt'$$

$$t'_i = t'_{i-1} + \Delta t'$$

Also, the oxide thickness values measured on the mouth of the crack using plastic replicas may be used to estimate the age of cracks.

In other embodiments, oxide thickness profiles are measured on crack surfaces of components and are used for estimating the rates of crack propagation and the age of cracks. The embodiments of the invention are particularly suitable for high-temperature components fabricated from metals and used in power plants. To implement this technique, it is necessary to fully characterize the kinetics of high-temperature oxidation in the metals used in the fabrication of these components. In this study, the oxidation characteristics of an American Society of Testing and Materials (ASTM) Grade P91 ferritic steel used in steam headers and piping is used as an example.

Two sets of studies were conducted. The first measured oxide thicknesses in polished rectangular specimens after exposure to high temperature for a range of temperatures and times to determine the oxidation kinetics. The oxidized samples were also subjected to SEM examination, and measurements of physical properties such as density were made. The second measured the oxide layer thickness on the fracture surfaces of creep-fatigue crack growth samples tested as part of a study where the crack growth rates were measured. The measured crack growth rates were compared to the predicted crack growth rates from models developed using the controlled oxidation test results. Good agreement was found between the measured crack growth rates and those predicted from oxide thickness measurements.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above-described embodiments, methods, and examples, but by all embodiments and methods within the scope and spirit of the disclosure.

What is claimed is:

1. A method to develop the age and history of a crack region of a specimen having an oxide layer thickness at the mouth of the crack region comprising the steps of: exposing the specimen to one or more predetermined temperature ranges that cover the designated service temperatures for varying periods ranging between 10 and 1000 hours; and measuring the thickness of the oxide layer at the crack mouth along the thickness direction.

2. The method of claim 1 wherein cracks are examined in reheat steam pipes, steam turbine rotors and casings, chemical reactors, turbine components, land-based turbine components, aircraft turbine components, and components fabricated from metals and used in power plants.

3. A method to estimate the age of a crack comprising the steps of:
using a replica of the cracked region to estimate the oxide thickness at the mouth of a crack.

4. The method of claim 3 wherein cracks are examined in reheat steam pipes, steam turbine rotors and casings, chemical reactors, turbine components, land-based turbine components, aircraft turbine components, and components fabricated from metals and used in power plants.

5. The method of claim 3 wherein the crack is excavated from the component and the oxide thickness profile measured so that the rate at which the crack was growing during service can be estimated.

6. The method of claim 3 wherein the full growth history of the cracks may be determined and then used to validate analytical models used to estimate remaining life and inspection intervals in components.

7. The method of claim 3 further including the steps of deriving the relationship between the oxide thickness measured on a crack surface and the associated time-history.

8. The method of claim 3 wherein cracks are examined in reheat steam pipes, steam turbine rotors and casings, chemical reactors, turbine components, land-based turbine components, aircraft turbine components, and components fabricated from metals and used in power plants.

9. The method of claim 3 further including the steps of deriving the relationship between the oxide thickness measured on a crack surface and the associated time-history.

10. A method to estimate the age of a cracked region in a component having an oxide layer thickness at the mouth of the cracked region comprising the steps of: excavating the cracked region from the component, fracturing the specimen to expose the cracked surface; applying a hard coating; sectioning the sample to reveal the oxide thickness profile of the oxide layer of the mouth of the cracked region; measuring the thickness of the oxide layer as a function of crack depth.

11. The method of claim 10 wherein the sample is sectioned in the middle to reveal the oxide thickness profile.

12. The method of claim 10, wherein oxide thickness, x, is measured as a function of crack where $x_0$=oxide thickness at the mouth of the crack.

13. The method of claim 10 wherein cracks are examined in reheat steam pipes, steam turbine rotors and casings, chemical reactors, turbine components, land-based turbine components, aircraft turbine components, and components fabricated from metals and used in power plants.

14. The method of claim 10 further including the steps of deriving the relationship between the oxide thickness measured on a crack surface and the associated time-history.

* * * * *